(12) United States Patent
Ausich et al.

(10) Patent No.: US 6,686,456 B2
(45) Date of Patent: Feb. 3, 2004

(54) METHOD FOR THE ELIMINATION OF KUNITZ AND BOWMAN-BIRK TRYPSIN INHIBITORS AND CARBOXYPEPTIDASE INHIBITOR FROM POTATO PROTEINS

(75) Inventors: Rod Ausich, Des Moines, IA (US); Fayad Z. Sheabar, West Des Moines, IA (US); Robert Stomp, Des Moines, IA (US); Clarence Ryan, Pullman, WA (US); Brent Davidson, Ankeny, IA (US)

(73) Assignee: Kemin Foods, L.C., Des Moines, IA (US)

( * ) Notice: Subject to any disclaimer, the term of this patent is extended or adjusted under 35 U.S.C. 154(b) by 0 days.

(21) Appl. No.: 09/900,550

(22) Filed: Jul. 6, 2001

(65) Prior Publication Data

US 2003/0092151 A1 May 15, 2003

(51) Int. Cl.[7] .............................. A23J 1/00; A23J 14/00; A61K 35/78; A61K 35/80; A61K 38/00
(52) U.S. Cl. ........................ 530/422; 530/412; 530/370; 424/725; 424/773; 514/2
(58) Field of Search ............................. 514/2; 530/412, 530/414, 370, 419, 422; 210/702, 704, 705; 930/240; 424/725, 195.1, 773

(56) References Cited

U.S. PATENT DOCUMENTS

| | | |
|---|---|---|
| 4,491,578 A | 1/1985 | Peikin |
| 4,906,457 A | 3/1990 | Ryan |
| 5,187,154 A | 2/1993 | Phillips et al. |
| 5,264,365 A * | 11/1993 | Georgiou et al. ......... 435/252.8 |
| 6,414,124 B1 | 7/2002 | Ryan et al. |

FOREIGN PATENT DOCUMENTS

| | | |
|---|---|---|
| EP | 0 487 480 A2 * | 5/1992 |
| WO | WO-09901474 | 1/1999 |
| WO | WO-0117541 | 8/2001 |

OTHER PUBLICATIONS

Burgess, R. Protein Purification Micro To Macro; 1987, Alan R. Liss Inc. New York, NY. pp. 308–309.*

Iwasaki et al. Purification And Partial Characterization Of Two Different Types Of Proteinase Inhibitors (Inhibitors II–A And II–B) From Potatoes; J. Biochem., 70, 1971, pp. 817–826.*

Kaufman et al. Molecular And Cellular Methods In Biology And Medicine; 1995, CRC Press, Inc., Boca Raton Fl. p. 42.*

Melville, J.C. And Ryan, C.A., "Chymotrypsin inhibitor I from potatoes", *J. Biological Chem.*, 1972, 247: p. 3445–3453.

Bryant, J., Green, T.R., Gurusaddaiah, T., And Ryan, C.A., "Proteinase inhibitor II from potatoes: Isolation and characterization of its protomer components", *Biochemistry*, 1976, 15: p. 3418–3424.

Armstrong, W.B., Kennedy, A.R., Wan, X.S., Atiba, J., McLaren, C.E., And Meyskens, F.L., Jr., "Single dose administration of Bowman–Birk inhibitor concentrate in patients with oral leukoplakia", *Cancer Epidemiol.*, 2000, 9: p. 43–47, Biomakers Prev.

Beekwilder, J., Schipper, B., Bakker, P., Bosch, D., And Jongsma, M., "Characterization of potato proteinase inhibitor II reactive site mutants", *Eur. J. Biochem.*, 2000, 267: p. 1975–1984.

Billings, P.C., St. Clair, W.H., Maki, P.A., And Kennedy, A.R., "Distribution of the Bowman–Birk protease inhibitor in mice following oral administration", *Cancer Lett.*, 1992, 62: p. 191–197.

Campos, F.A.P. And Richardson, M., "The complete amino acid sequence of the bifunctional α–amylases/trypsin inhibitor from seeds of ragi (Indian finger millet; Eleusine coracana Goertn)", *FEBS Lett.*, 1983, 152: p. 300–304.

Campos, F.A.P. And Richardson, M., "The complete amino acid sequence of α–amylases inhibitor from seeds of ragi (Indian finger millet; Eleusine coracana Goertn)", *FEBS Lett.*, 1984, 167: p. 221–225.

Duan, X., Li, X., Xue, Q., Abo–El–Saad, M., Xu, D., And Wu, R., "Transgenic rice plants harboring an introduced potato proteinase inhibitor II gene are insect resistant", *Nat. Biotechnol.*, 1996, 14: p. 494–498.

Hass, G.M., Hermodson, M.A., Ryan, C.A., And Gentry, L., "Primary structures of two low molecular weight proteinase inhibitors from potatoes", Biochemistry, 1982, 16, 21: p. 752–756.

Hill, A.J., Peikin, S.R., Ryan, C.A., And Blundell, J.E., "Oral administration of proteinase inhibitor II from potatoes reduces energy intake in man", *Physiol. Behav.*, 1990, 48: p. 241–246.

(List continued on next page.)

*Primary Examiner*—Patricia Patten
(74) *Attorney, Agent, or Firm*—Kent Herink; Daniel Rosenberg; Davis Law Firm

(57) ABSTRACT

A method for removing protein impurities from extracts of protease inhibitor-containing plant material. Plant materials containing protease inhibitors, such a potato tubers that contain protease inhibitor II, are extracted using an alcohol-free solvent. The proteins present in the extract include impurities other than the protease inhibitor, specifically Kunitz, Bowman-Birk and carboxypeptidase inhibitors. The extract is subjected to heat treatment to denature and precipitate the unstable protein impurities followed by centrifugation to remove the precipitate. Ultrafiltration in the presence of a buffer removes the Bowman-Birk and carboxypeptidase inhibitors. The resulting purified protease inhibitor has applicability in the control of obesity and diabetes.

4 Claims, 4 Drawing Sheets

OTHER PUBLICATIONS

Huang, C., Ma, W.Y., Ryan, C.A., And Dong, Z., "Proteinase inhibitors I and II from potatoes specifically block UV-induced activator protein-1 activation through a pathway that is independent of extra cellular signal regulated kinases, c-Jun N-terminal kinases, and P38 kinase", *Proc. Natl. Acad. Sci.*, 1997, 94: p. 11957–11962.

Iwasaki, T., Kijohara, T., And Yoshikawa, "Chemical and Physichemical Characterization of Two Different types of Proteinase Inhibitors (inhibitors#– a and (II –b) from Potatoes." *J. Biol. Chem.*, 1972, 72: p. 1029, Tokyo.

Keil, M., Sanchez-Serrano, J., Schell, J., And Willmitzer, L., "Primary structure of a proteinase inhibitor II gene from potato (*Solanum tuerosum*)", *Nuc. Acids Res.*, 1986, 14: p. 5641–5650.

Larionova, N.I., Balabushevich, N.G., Gladysheva, I.P., Moroz, N.A. Kazanskaia, N.F., Polekhina, O.V., And Donetskii, I.A., "Natural proteinase inhibitors as a basis for creating new drugs", *Vopr. Med. Khim*, 1994, 40: p. 25–31.

Li, N., Qu, L.J., Liu, Y., Li, Q., Gu, H., And Chen, Z., "The refolding, purification, and activity analysis of a rice Bowman–Birk inhibitor expressed in *Escherichia coli*", *Purification Expr. Purif.*, 1999, 15: 99–104.

Mitsumori, C., Yamagishi, K., Fujino, K., And Kikuta, Y., "Detection of immunologically related Kunitz and Bowman–Birk proteinase inhibitors expressed during potato tuber development", *Plant Mol. Biol.*, 1994, 26: p. 961–969.

Murray, C. and Christeller, J.T., "Genomic nucleotide sequence of a proteinase inhibitor II gene", *Plant Physiol.*, 1994, 106: p. 1681.

Otsuki, M., Tani, S., Fujii, M., Nakamura, T., Okabayashi, Y., And Koide, M., "Differential effects of proteinase inhibitor camosat on exocrine pancreas in fed and fasted rats", *Am. J. Physiol.*, 1993, 265 (Regulatory Integrative Com. Physiol. 34): R896–R901.

Pena–Cortes, H., Sanchez–Serrano, J., Prat, S., And Willmitzer, L., "Signals involved in the wound–induced expression of the proteinase inhibitor II gene of potato", *Biochem. Soc. Symp.*, 1994, 60: 143–148.

Phillips, W.T. And Schwartz, J.G., "Decelerating gastric emptying: therapeutic possibilities in type 2 diabetes", *Diabetes Med.*, 1996, 12: S44–48.

Plunkett, G. And Ryan, C.A., "Reduction and carboxamidomethylation of the single disulfide bond of proteinase inhibitor I from potato tubers. Effects on stability, immunological properties, and inhibitory activities", *J. Biol. Chem.*, 1980, 255: 2752–2755.

Pusztai, A., Grant, G., Bardocz, S., And Baintner, K., "Both free and complexed trypsin inhibitors stimulate pancreatic secretion and change duodenal enzyme levels", *Am. J. Physiol.*, 1997, 272 (Gastrointestinal Liver Physiol. 35): G340–G350.

Reddy, C.S. And Hayes, W.A., *Food Born Toxicants in Principles and Methods of Toxicology*, 1994, p. 321–360, $3^{rd}$ Edition, Edited by Hayes, A.W., Raven Press, New York, US.

Reseland, J.E., Holm, H., Jacobsen, M.B., Jenssen, T.G., And Hanssen, L.E., "Proteinase inhibitors induce selective stimulation of human trypsin and chymotrypsin secretion", *J. Nutr.*, 1996, 126: p. 634–642.

Ryan, C.A., "Proteinase Inhibitors", *In The Biochemistry of Plants*, 1981, p. 351–370, vol. 6, Academic Press.

Ryan, C.A. And Walker–Simmons, M., "Plant Proteinase", *In The Biochemistry of Plants*, 1981, vol. 6, p. 321–350, Academic Press.

Schwartz, J.G., Guan, D., Green, G.M., And Phillips, W.T., "Treatment with an oral proteinase inhibitor slows gastric emptying and actually reduces glucose and insulin levels after a liquid meal in type II diabetic patients", *Diabetes Care*, 1994, 17: p. 255–262.

Sanchez–Serano, J., Schmidt, R., Schell, J., And Willmitzer, L., "Nucleotide sequence of proteinase inhibitor II encoding DNA of potato (*Solanum tuberosum*) and its mode of expression", *Mol. Gen. Genet*, 1986, 203: p. 15–20.

Sang–Gon Suh, Peterson, J.E., Stiekema, W.J., And Hannapel, D.J., "Purification and characterization of the 22–kilodalton potato tuber proteins", *Plant Physiol.*, 1990, 94: p. 40–45.

Sugiyama, M., Atomi, Y., Wada, N., Kuroda, A., And Muto, T., "Effecto of oral protease inhibitor administration on gallbladder motility in patients with mild chronic pancreatitis", *J. Gastroenterol*, 1997, 32: p. 374–379.

\* cited by examiner

METHOD FOR THE ELIMINATION OF KUNITZ AND BOWMAN-BIRK TRYPSIN INHIBITORS AND CARBOXYPEPTIDASE INHIBITOR FROM POTATO PROTEINS

BACKGROUND OF THE INVENTION

1. Field of the Invention

The invention relates generally to the removal of proteinase inhibitors from plant sources and, more specifically, to the removal of Kunitz and Bowman-Birk trypsin inhibitors and carboxypeptidase inhibitors from proteins extracted from potato tubers.

2. Background of the Prior Art

Proteins that inhibit proteolytic enzymes are often found in high concentrations in many seeds and other plant storage organs. Inhibitor proteins are also found in virtually all animal tissues and fluids. These proteins have been the object of considerable research for many years because of their ability to complex with and inhibit proteolytic enzymes from animals and microorganisms. The inhibitors have become valuable tools for the study of proteolysis in medicine and biology. Protease inhibitors are of particular interest due to their therapeutic potentials in controlling proteinases involved in a number of disorders such as pancreatitis, shock, and emphysema, and as agents for the regulation of mammalian fertilization. Potato tubers are a rich source of a complex group of proteins and polypeptides that potently inhibit several proteolytic enzymes usually found in animals and microorganisms. In particular, potato inhibitors are known to inhibit human digestive proteinases, and thus have application in the control of obesity and diabetes.

Proteinase inhibitors found in plants are typically polypeptides and proteins that are composed entirely of L-amino acids through peptide bonds. These proteinase inhibitors differ significantly in their properties. The association of natural proteinase inhibitors with the proteinases that they inhibit is strong at neutral pH, and association constants are usually in the range of $10^7$–$10^{14}$ $M^{-1}$. Such associations are pH-dependent, and they decrease rapidly as the pH is lowered from neutrality to 3 (Ryan, C. A., and Walker-Simmons, M. 1981. Plant Proteinase. In *The Biochemistry of Plants*, V6, pp. 321–350, Academic Press).

Plant proteinase inhibitors generally are quite stable molecules and are often resistant to heat, pH extremes, and proteolysis by proteinases, even by those they do not inhibit. This stability has been attributed in part to the high degree of cross-linking through disulfide bridges. Other, non-covalent interactions also contribute significantly to the stability of the inhibitors. For example, protease inhibitor I from potatoes is a powerful chemotrypsin inhibitor that, while stable in solution at 80° C. for several minutes (Melville, J. C., and Ryan, C. A. Chemotrypsin inhibitor I from potatoes. *J. Microb. Chem.* 247: 3445–3453, 1972), contains only one disulfide bond per monomer unit (MW ~8,300) that can be reduced and carboxymethylated without loss of inhibitory activity (Plunkett, G., and Ryan, C. A. Reduction and carboxamidomethylation of the single disulfide bond of proteinase inhibitor I from potato tubers. Effects on stability, immunological properties, and inhibitory activities. *J. Biol. Chem.*, 255: 2752–2755, 1980).

Several proteinases exhibit substrate specificity, whereas others, such as papain, have broad substrate specificity. Specific proteinase inhibitor families were identified for each of the four mechanistic classes of proteolytic enzymes, i.e., serine, cysteinyl, aspartyl and metallo-proteases (Ryan, C. A. Proteinase Inhibitors. In The Biochemistry of Plants, V6, pp.351–370, Academic Press). In other circumstances, identical abundant proteins were capable of inhibiting enzymes of various families and have very different substrate specificity, such as the inhibitors of both proteinases and α-amylases which were isolated from cereal seeds (Campos, F. A. P., and Richardson, M. The complete amino acid sequence of α-amylases/trypsin inhibitor from seeds of ragi (Indian finger millet; *Eleusine coracana* Goertn.). FEBS Lett., 152: 300–304, 1983; Campos, F. A. P., and Richardson, M. The complete amino acid sequence of α-amylases/trypsin inhibitor from seeds of ragi (Indian finger millet; *Eleusine coracana* Goertn.). FEBS Lett., 167: 221–225, 1984).

Two broad classes of protease inhibitor superfamilies have been identified from soybean and other legumes with each class having several isoinhibitors. Kunitz-type inhibitor is the major member of the first class whose members have 170–200 amino acids, molecular weights between 20,000 and 25,000, and act principally against trypsin. Kunitz-type proteinase inhibitors are mostly single chain polypeptides with 4 cysteines linked in two disulfide bridges, and with one reactive site located in a loop defined by disulfide bridge. The second class of inhibitors contains 60–85 amino acids, has a range in molecular weight of 6000–10,000, has high proportion of disulfide bonds, is relatively heat-stable, and inhibits both trypsin and chemotrypsin at independent binding sites. Bowman-Birk inhibitor is an example of this class.

Kunitz inhibitor is capable of inhibiting trypsin derived from a number of animal species as well as bovine chemotrypsin, human plasmin, and plasma kallikrein. The cationic form of human trypsin, which accounts for a majority of trypsin activity, is only weakly inhibited by the Kunitz inhibitor, whereas the anionic form is fully inhibited.

The Bowman-Birk inhibitor is a 71 amino acid chain protein with 7 disulfide bonds characterized by its low molecular weight of about 8000 (in non-associated monomers), high concentration (about 20%) of cystine, high solubility, resistance to heat denaturation and having the capacity to inhibit trypsin and chymotrypsin at independent inhibitory sites.

The major effects of proteinase inhibitors in animal diets include growth depression and pancreatic hypertrophy. Resistance of raw soybean protein to proteolysis, low levels of sulfur-containing amino acids in soybean proteins, and lower digestibility, absorption, and utilization of available nitrogen from the small intestine due to the presence of proteinase inhibitors, all appear to contribute to growth depression.

Proteinase inhibitors extracted from potatoes have been distinguished into two groups based on their heat stability. The group of inhibitors that is stable at 80° C. for 10 minutes have been identified as inhibitor I (mol. wt. 39,000) (Melville et al.), carboxypeptidase inhibitor (CPI) (mol. wt. 4,100) (Ryan, C. L., Purification and properties of a carboxypeptidase inhibitor from potatoes. *J. Biol. Chem.* 249: 5495–5499, 1974), inhibitors IIa and IIb (mol. wt. 20,700) (Bryant, J., Green, T. R., Gurusaddaiah, T., Ryan, C. L. Proteinase inhibitor II from potatoes: Isolation and characterization of its protomer components. *Biochemistry* 15: 3418–3424, 1976), and inhibitor A5 (mol. wt. 26,000).

Separation of proteinase inhibitor I by ion exchange chromatography on sulfoethylcellulose in the presence of 0.1 M formic acid in 8 M urea resolved two major and two minor inhibitor protomers. Reassociation by dilution to the tetramer form resulted in two major protomers. The first protomer was shown to be a powerful inhibitor of both chymotrypsin and trypsin. The second protomer was shown to strongly inhibit chymotrypsin but only weakly inhibit trypsin. All four purified promoters resolved from Inhibitor I can be reassociated either individually or hybridized with each other to form tetrameric isoinhibitors. All of the tetrameric inhibitor I species prepared from each of the four protomeric types have glutamic acid at the $NH_2$ terminal. However, they differ from each other in amino acid composition, electrophoretic mobility, reactivity with chymotrypsin and trypsin, and digestibility with pepsin.

Proteinase inhibitor II, an inhibitor of chemotrypsin and trypsin, which are serine proteases, is also a heat stable protein. It has a dimeric molecular weight of 21,000. Four monomeric isoinhibitor species of molecular weight 10,500 comprise inhibitor II and have been isolated by chromatography in the presence of urea. Upon removal of the urea, each monomeric species dimerized to yield homogenous dimers. The three major protomer species, called B, C, and D were found to have similar molecular weights and amino acid compositions, and each has an N-terminal alanine residue. Reconstituted dimers possess two binding sites for bovine α-chymotrypsin, indicating that each monomer possesses one binding site for this enzyme. Significant differences have been noted among the reconstituted dimers in their isoelectric points, immunoelectrophoretic mobilities, ion-exchange properties, and their inhibitory reactivities against trypsin. The properties of the inhibitor II dimeric species are similar but not identical to inhibitors IIa and IIb reported from Japanese potatoes, indicating the existence of intervarietal, as well as intravarietal, differences among potato tuber inhibitor II isoinhibitors (Bryant et al.).

Protease inhibitor II is composed of two sequence repeats. It contains two reactive site domains. The role of the two reactive sites in the inhibition of trypsin and chemotrypsin has been evaluated. The first reactive site inhibits only chymotrypsin ($Ki=2$ nM), and this activity is very sensitive to mutations. The second reactive site strongly inhibits trypsin ($Ki=0.4$ nM) and chemotrypsin ($Ki=0.9$ nM), and is quite stable towards mutations (Beekwilder, J., Schipper, B., Bakker, P., Bosch, D., and Jongsma, M. Characterization of potato proteinase inhibitor II reactive site mutants. *Eur. J. Biochem.*, 267: 1975–1984, 2000).

In addition to inhibitor I and inhibitor II, several low molecular weight inhibitors have been detected in potato. Among them are the carboxypeptidase inhibitor, which has been extensively characterized (Bryant et al., 1976 and Iwasaki, T., Kijohara, T., and Yoshikawa. *J. Biol. Chem.* (Tokyo) 72: 1029, 1972) and at least three inhibitors of serine proteinases. The amino acid sequences of two low molecular weight serine proteinase inhibitors from Russet Burbank potatoes have been determined. One of those, a chemotrypsin inhibitor, is a peptide of 52 amino acid residues, while the second inhibitor, which is specific for trypsin, contains 51 amino acid residues. These peptides are highly homologous, differing at only nine positions. At position 38, the chymotrypsin inhibitor possesses leucine and the trypsine inhibitor an arginine. The inhibitors are also homologous with potato inhibitor II and with an inhibitor previously isolated from eggplants (Hass, et al., 1982).

U.S. Pat. No. 5,187,154 describes a method for the diagnosis and the treatment of individuals with diabetes or at risk to develop diabetes mellitus. In particular, gastric emptying determinations are used to assess risk. Risk or early symptoms associated with subsequent development of diabetes mellitus may be controlled or alleviated by delaying gastric emptying, which was achieved by the administration of cholecystokinin.

U.S. Pat. No. 4,906,457 describes compositions and methods for reducing the risk of skin cancer. The described compositions included at least one effective protease inhibitor. Preferred protease inhibitors included serine protease inhibitors and metallo-protease inhibitors. The protease inhibitors were preferably included in concentrations ranging from approximately 10 picograms to 10 milligrams per milliliter of the skin-applicable topical mixtures. The topical mixtures preferably included a suitable topical vehicle such as a cream, lotion, or ointment. One class of anti-carcinogenic skin treatment compositions of this invention preferably included the desired protease inhibitors in combination with a suitable sunscreen agent or agents, such as para-amino benzoic acid, to provide particularly advantageous compositions for reducing the risk of sunlight-induced skin cancer.

When applied to mouse epidermal JB6 cells, proteinase inhibitors I and II from potatoes blocked the UV induced transcription factor activator protein-1 (AP-1), which has been shown to be responsible for the tumor promoter action of UV light in mammalian cells. The inhibition appears to be specific for UV induced signal transduction for AP-1 activation. Furthermore, the inhibition of UV induced AP-1 activity occurs through a pathway that is independent of extracellular signal-regulated kinases and c-jun N-terminal kinases as well as P38 kinases (Huang, C., Ma, W. Y., Ryan, C. A., Dong, Z. Proteinase inhibitors I and II from potatoes specifically block UV-induced activator protein-1 activation through a pathway that is independent of extracellular signal regulated kinases, c-jun N-terminal kinases, and P38 kinase. *Proc. Natl. Acad. Sci.*, US, 94: 11957–11962, 1997).

U.S. Pat. No. 4,491,578 describes a method of eliciting satiety in mammals through the administration of an effective amount of a trypsin inhibitor. The method was based on the postulate that the enzyme trypsin, normally secreted by the pancreas, constitutes a negative feedback signal for cholecystokinin secretion that in turn comprises a putative satiety signal. Thus, the effect of the trypsin inhibitor is to increase the concentration of cholecystokinin secretion advancing the sensation of satiety resulting in a consequent decrease in food intake and, over time, body weight.

The effect of PI2 extracted from potatoes, which increases CCK release, or food intake was examined in 11 lean subjects. Five minutes before presenting them with a lunchtime test meal, volunteers received 1.5 g PI2 in a high protein soup vehicle (70 kcal), the soup vehicle alone, or a no-soup control, according to a double blind, within subject design. The consumption of the soup alone led to a non-significant 3% reduction in energy intake. The addition of 1.5 g PI2 to the soup significantly reduced energy intake by additional 17.5%. Pre-meal ratings of motivation to eat and food preferences did not predict the reduction in energy intake by the proteinase inhibitor. Based on the results, the authors concluded that endogenous CCK may be have an important role in the control of food intake and that proteinase inhibition may have a potential for reducing food intake (Hill et al., 1990). Clinical trials on potato extracts containing Kunitz inhibitors showed no effect on satiety.

The efficiency of oral trypsin/chemotrypsin inhibitor in delaying the rate of gastric emptying in recently diagnosed type II diabetic patients and improving their post-prandial metabolic parameters have been examined (Schwartz, J. G., Guan, D., Green, G. M., Phillips, W. T. Treatment with an oral proteinase inhibitor slows gastric emptying and actually reduces glucose and insulin levels after a liquid meal in type II diabetic patients. *Diabetes Care*, 17: 255–262, 1994). Serum insulin, plasma glucose, plasma gastric inhibitory polypeptide levels, and the rate of gastric emptying were all significantly decreased over the 2 hour testing period in subjects who received proteinase inhibitor in their oral glucose/protein meal. U.S. Pat. No. 5,187,154 suggests the administration of CCK through an intramuscular injection or an intranasal spray. Alternatively, an oral administration of an agent that enhances endogenous release of CCK could represent an important approach to the treatment of Type 2 diabetes. One of the agents that may have a therapeutic application in patients with recently diagnosed Type 2 diabetes can be the potato proteinase inhibitor II.

Others have attempted to remove impurity proteins by the use of chromatography, including ion exchange, gel-filtration and affinity (Mellville et al.), ethanol protein solution (Bryant et al.), and precipitation with salt and solvents followed by dialysis (Pearce, G. and Ryan, C. A. A rapid, large-scale method for the purification of metallo-carboxypeptidase from potato tubers. Anal. Biochem. 30: 223–225, 1983). These methods can not be practiced feasibly on a production scale.

SUMMARY OF THE INVENTION

The invention consists of a process which utilizes heat treatment of potato proteins in the presence of salt, followed by centrifugation and filtration, as an efficient method for the elimination of Kunitz family, Bowman-Birk proteinase and carboxypeptidase inhibitors from other potato proteinase inhibitors. Raw potatoes are mixed with an organic acid, preferably formic acid, and a salt, preferably sodium chloride. The mixture is comminuted to reduce the size and increase the surface area of potato particles. The soluble proteins, including PI1, PI2, Kunitz family, Bowman-Birk and carboxypeptidase inhibitors, are released into the liquid phase and the mixture is centrifuged to remove solids.

The supernatant is incubated at a temperature of between about 60° C. and about 80° C., and preferably between about 70° C. and 73° C., for between about 30 minutes and about 180 minutes, and preferably between about 45 minutes and 75 minutes, to denature the impurity proteins without denaturing PI2. The solubility of the impurities was further reduced by lowering the temperature of the heat-treated material to between about 20° C. and about 30° C., and preferably between about 25° C. and about 26° C., at which temperatures PI2 remains soluble in the supernatant.

Centrifugation for 500,000 g-seconds or longer is used to remove the denatured impurity proteins from the heat-treated supernatant. Ultrafiltration using a cellulosic or sepharose membrane combined with diafiltration against an ammonium bicarbonate buffer is used to remove the carboxypeptidase inhibitor.

The process of the present invention is highly efficient in the separation and removal of Kunitz type inhibitor, previously found to interfere with the satiety efficacy of the PI2 in humans, as well as Bowman-Birk and carboxypeptidase inhibitors. The process also provides high recovery and yield of the PI2 inhibitor, increasing the concentration of PI2 in the final product by more than 100 times in comparison to its concentration in the proteins fraction in the raw potatoes. The process is efficient at laboratory, pilot plant and production scales, is easy to perform and does not require specialized equipment.

DETAILED DESCRIPTION OF A PREFERRED EMBODIMENT

Figure 1:
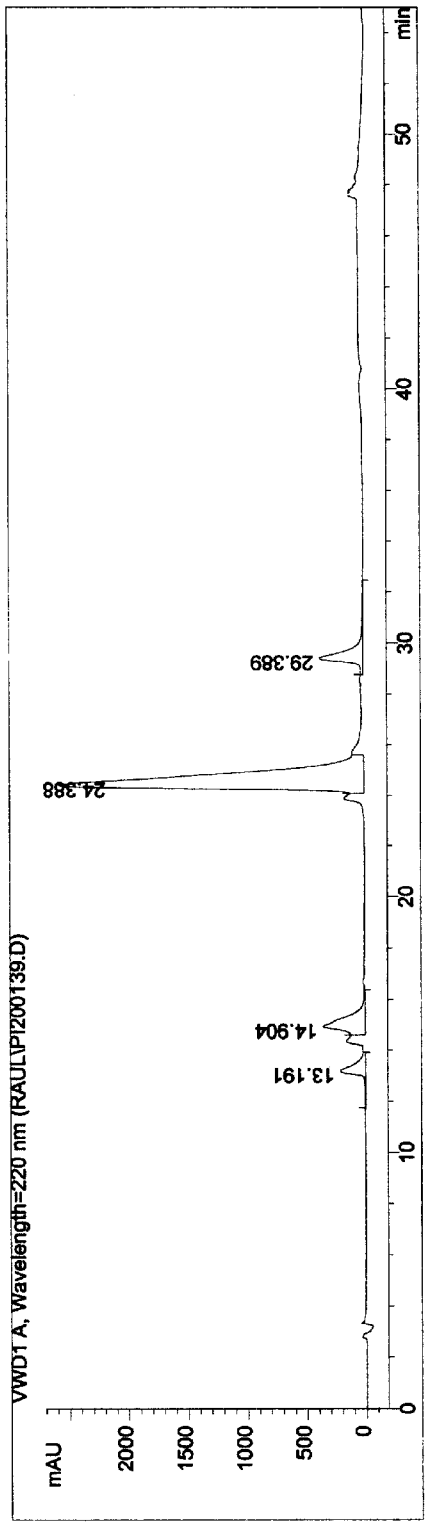
FIG. 1 is a chromatogram of a Kunitz inhibitor standard made using reverse phase HPLC.

The efficacy of potato PI2 to function as a satiety aid was studied in a clinical trial in which the PI2 had a protein purity of not less than 50%. Unfortunately, extracting PI2 from potatoes results in the concomitant extraction of impurities, including proteins such as Kunitz, Bowman-Birk, and carboxypeptidase inhibitors. Since certain of these impurities are believed to interfere with the efficacy of PI2, a process for their removal is needed.

PI2 is known to have significant heat stability in comparison with certain other soluble proteins found in potatoes. Through the use of heat treatment, protein impurities that are less heat stable can be eliminated from the liquid phase by heating the extract to a temperature and for a time period sufficient to denature the non-stable proteins without substantially denaturing the PI2, followed by removal of the denatured proteins. An experiment was conducted to examine the maximum temperature of the heat-treatment step, the hold-time at the elevated temperature, and a cooling temperature that was expected to reduce the solubility of the denatured proteins so that they can be removed from the solution. At the same time, loss of soluble PI2, removal of soluble non-PI2 proteins, and precipitation of insoluble materials were examined. The majority of the undesirable, non-stable proteins are believed to be Kunitz type proteins. In using the high-performance liquid chromatography (HPLC) methodology applicable for PI2 quantification, the Kunitz type impurities are those proteins which elute following the target PI2 protein and the carboxypeptidase inhibitor.

The carboxypeptidase inhibitor (CPI) is shown to have heat-stability similar to PI2 as observed by the limited loss of this impurity during the heat-treatment step. While the heat stability of the Bowman-Birk impurities is not well-characterized, it has been assumed that some or all may not be denatured during the heat treatment step and so, like the carboxypeptidase inhibitor, must be removed by a different method. Given the difference in molecular weight between the Bowman-Birk (approx. 8000 Daltons) and carboxypeptidase inhibitor (approx. 4100 Daltons) compared to PI2 (approx. 21,700 Daltons), molecular size-based separation techniques were investigated.

Extraction and Purification Process

The extraction and isolation of PI2 from potatoes begins with the addition of an organic acid, preferably formic acid, and a salt, preferably sodium chloride, to raw potatoes. The mixture is subjected to comminution to increase the surface area of the potato particles and improve the extraction of soluble proteins. Centrifugation is used to remove solids, and the liquid fraction is heated at a temperature sufficient to denature many undesired proteins but not PI2. The solution is again centrifuged to remove the insoluble denatured proteins and the liquid fraction is microfiltered to remove relatively large particles. Ultrafiltration is used to further purify the PI2 in the retentate.

More specifically, whole, raw potatoes are added to an aqueous solvent containing formic acid and sodium chloride. The potatoes and solvent are comminuted to reduce the potato particle size and increase the exposed surface area to improve extraction efficiencies. A filter centrifuge is used to remove bulk fiber and starch while retaining the soluble proteins in the liquid fraction. The filtrate is heated to less than 80° C. for between about 30 minutes and 3 hours and then cooled to approximately 25° C. A tubular bowl clarifier is used to remove the non-heat stable impurities, notably the Kunitz inhibitors. A microfilter (0.3 m) is used to remove particles not removed by the clarifier. Ultrafiltration using a filter having a molecular weight cutoff of between approximately 5000 and 10,000 Daltons in the presence of a diafiltration buffer, preferably ammonium bicarbonate, is used to remove impurities generally smaller than the molecular weight cutoff, notably the Bowman-Birk and carboxypeptidase inhibitors. The retentate contains purified PI2 and may be lyophilized to generate a dried product.

Even more specifically, whole, raw potatoes, preferably those having a high PI2 content, are added to an extractant solution or solvent, comprising water with a sodium chloride content of between 0.3 N and 2.0 N to which is added between 0.5 and 2.5 weight percent formic acid, at a weight ratio of between 1:1 and 1:10 raw potatoes to solvent, and preferably about 1:2.5. A grind profile which results in an average particle size of approximately 500 m is used to create a relatively finely comminuted product without unduly heating of the slurry. The filter centrifuge uses a 35 m bag mesh set at approximately 75% load. Heat is applied to bring the liquid extract to a temperature of approximately 70° C. for approximately one hour. Cooling the extract to between 20° C. and 26° C. causes precipitation of the denatured proteins while the PI2 remains in solution. Centrifugation at approximately 13,000×g removes the denatured proteins. The clarifier is operated to reduce the weight percent of solids to about 0.01% or below. A cellulosic, open, screen channel membrane with a molecular weight cutoff of approximately 10,000 Daltons is used at a flow rate of 0.40 liters per minute per square foot of membrane surface, with a 20 psi pressure differential. Six volumes of 100 mM ammonium bicarbonate buffer are used in the diafiltration.

Reverse Phase HPLC Method

The amount of PI2, Kunitz and carboxypeptidase inhibitors was measured using reverse phase HPLC. A Microsorb C-18 column (4.6 mm×250 mm, 5 μm particles with 300 Angstrom pore size; Varian Analytical Instruments) was used. Two mobile phase solvents were prepared, solvent A was 800 g deionized $H_2O$, 150 g acetonitrile, and 0.95 g trifluoroacetic acid, and solvent B was 850 g acetonitrile and 0.85 g trifluoroacetic acid. Approximately 50 mg of the sample was added to 100 ml of solvent A. The sample was vortexed for 30 seconds, and then centrifuged at 10,000 rpm for 10 minutes. The supernatant was collected for RP-HPLC analysis. One hundred μl of the sample was injected into the column, with the pump set at 800–2500 psig, and a temperature of 30.0° C. The other flow rate, time, and solvent compositions are as set out in Table 1. The diode array of the detector was set at 220 nm.

TABLE 1

HPLC Conditions

| Time (min) | Flow rate (ml/min) | Solvent Composition (volume %) |
|---|---|---|
| 0 | 1 | 100% A |
| 5 | 1 | 100% A |
| 34 | 1 | 38% A |
| 38 | 1 | 100% B |
| 40 | 2 | 100% B |
| 45 | 2 | 100% B |
| 50 | 1 | 100% A |
| 55 | 1 | 100% A |

An external standard was prepared to construct a standard curve for calibration of the column. Five mg of BSA were dissolved in 10 ml of solvent A. Four volumes, i.e., 25, 50, 75, and 100 μL, were injected into the column. A calibration curve was generated from the results.

Gel Filtration Chromatography HPLC for the Purification of PI2

A method was developed to separate PI2 from other heat stable potato proteins using gel filtration high-performance liquid chromatography. A Shodex protein KW-803 column (8 mm×300 mm, 5 μm particles with 120 Angstrom pore size) was used. An isocratic 0.025 M phosphate buffer was used, and the flow rate was set to 0.25 ml/min, and the pressure maintained at 40 bar. The diode array of the detector was set at 220 nm. A 1 L volume of a 0.025 M potassium phosphate buffer, pH 7.0, was prepared for use as the mobile phase by adding 2.67 g $K_2HPO_4$ and 1.31 g of $K_2H_2PO_4$ to 900 ml of deionized water. After verification of a pH of 7.0, or adjustment to 7.0 using either HCl or NaOH, additional water is added to bring the volume to 1 L. The following HPLC gradient was used to flush the 5 ml manual injector sample loop.

TABLE 2

HPLC Conditions

| Time (min) | Flow rate (ml/mm) |
|---|---|
| 0 | 0.5 |
| 10 | 0.5 |
| 12 | 0.25 |

Kunitz and Carboxypeptidase Standards

Figure 3:
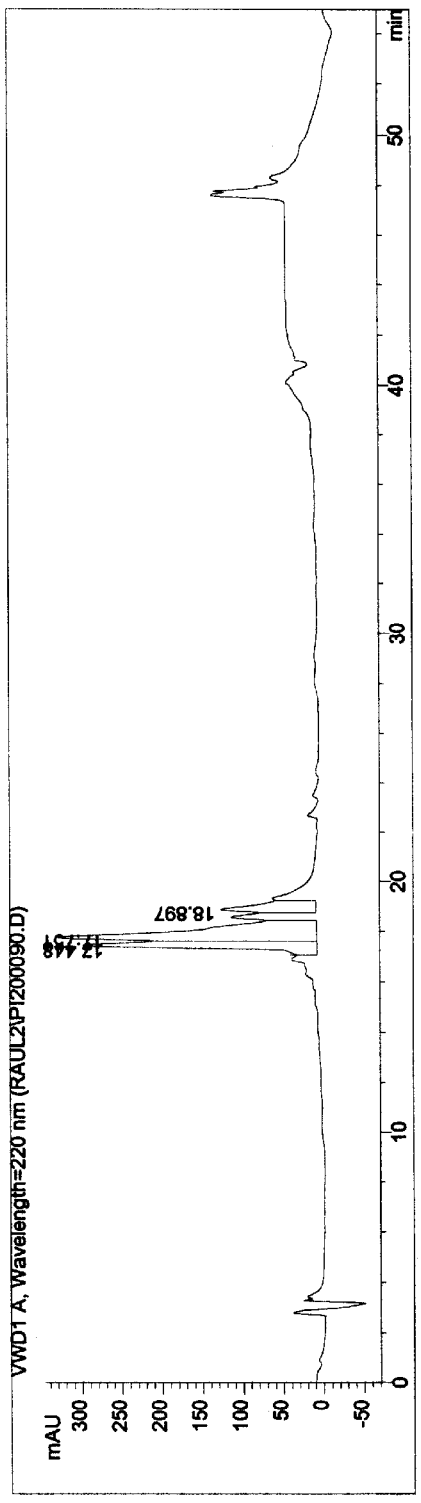
FIG. 3 is a chromatogram of a carboxypeptidase inhibitor standard made using reverse phase HPLC.

To establish the removal of Kunitz and carboxypeptidase impurities from the potato extract, the reverse phase HPLC method was used on commercially available Kunitz and carboxypeptidase standards. Both standards were purchased from SIGMA. A chromatogram of the Kunitz standard is illustrated in FIG. 1 and a chromatogram of the carboxypeptidase standard is illustrated in FIG. 3. Note that the major peak of the Kunitz impurities appears at 24.4 minutes, and the major peaks of the carboxypeptidase impurities appear at 17.4–17.8 and 18.9 minutes.

Bowman-Birk Standard

Figure 2:
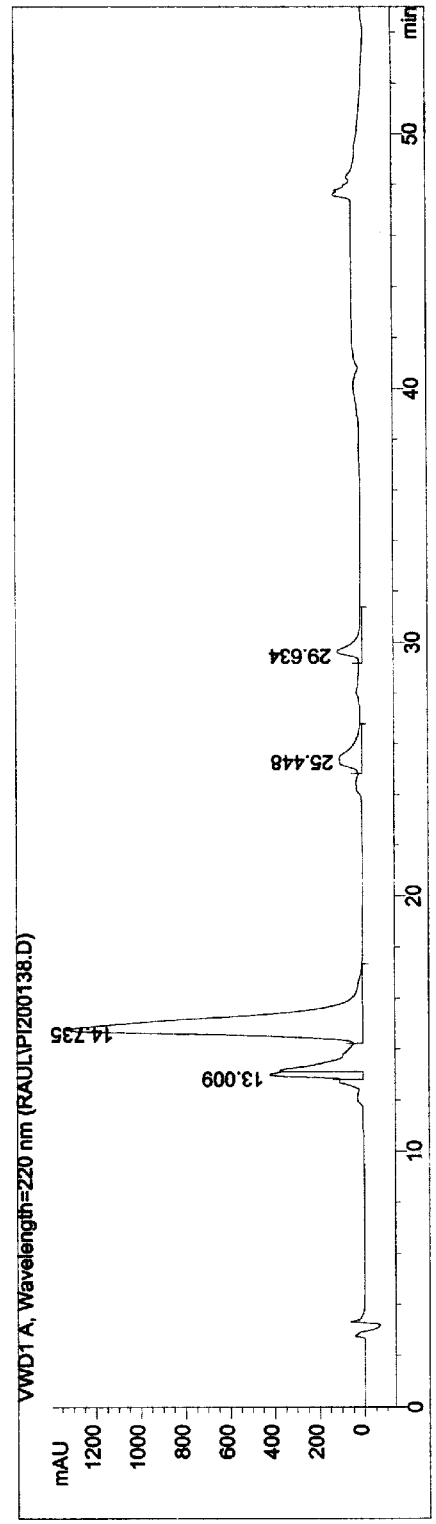
FIG. 2 is a chromatogram of a Bowman-Birk inhibitor standard made using reverse phase HPLC.

A commercially available Bowman-Birk standard was purchased from SIGMA and analyzed using the reverse phase HPLC method. A chromatogram of the Bowman-Birk standard is illustrated in FIG. 2. Note that the major peaks occur at 13 and 14.8 minutes.

Gel Electrophoresis Method

Gel electrophoresis used to analyze samples described in this application refers to the method described in "Separation Technique File No. 110, the Amersham Pharmacia LKB PhastSystem.

Trypsin Inhibition Assay

To further support the HPLC results indicating the presence of PI2, trypsin inhibition was applied as a biomarker for the efficiency of the extraction of PI2. A method was developed to assay the amount of trypsin inhibition demonstrated by the extracts of the present invention. The materials used included Trizma pre-set crystals, Trypsin (Worthington Biochemical LS003703), Nα-p-Tosyl-L-arginine methyl ester (TAME)(Sigma T-4626), and Trypsin Inhibitor (Sigma catalog #T-9003).

A hydrochloric acid solution, (0.001N) was prepared by mixing 81 µl of concentrated HCl and 1L of deionized $H_2O$. Tris buffer was prepared by mixing 1.74 g of Trizma pre-set crystals (pH 8.3) and 0.42 g calcium chloride in 250 ml of DI $H_2O$. Trypsin stock solution was prepared by dissolving 7.5 mg of trypsin in 5 ml of 0.001 N HCl. The concentration of trypsin in the solution was determined by measuring the absorbance at 280 nm.

$$[Trypsin](mg/ml) = A_{280} * 0.70$$

Twenty µl of the trypsin stock solution were added to 1.98 ml of 0.001N HCl to make the trypsin working solution. Trypsin solutions were kept on ice. A trypsin solution was freshly prepared after the $5^{th}$ or $6^{th}$ sample set if more than 6 samples were to be analyzed, since the trypsin activity diminishes over the period of time needed for analysis. TAME (38 mg) was dissolved in 10 ml 0.001 N HCl. This solution was freshly made on a daily basis.

A PI2 stock solution was prepared by dissolving 35.0 mg of sample in 10 ml of DI $H_2O$. This sample was also used for the protein assay. In addition, a 3.5 mg trypsin inhibitor (TI) sample (Sigma catalog #T-9003) was prepared in 10 ml DI $H_2O$. The sample was vortexed until completely dissolved, and then centrifuged for 10 min at 10,000 rpm. The supernatant served as the PI-2 or TI stock solution used for the preparation of PI2 or TI working solutions (Tables 3 and 4).

The following PI2 working solutions were prepared:

TABLE 3

| Working Solution | PI2 stock solution (µl) | 0.001 N HCl (µl) |
| --- | --- | --- |
| A | 25 | 1975 |
| B | 50 | 1950 |
| C | 75 | 1925 |
| D | 100 | 1900 |
| E | 300 | 1700 |
| F | 500 | 1500 |

The following TI std working solutions were prepared:

TABLE 4

| Working Solution | TI stock solution (µl) | 0.001 N HCl (µl) |
| --- | --- | --- |
| A | 25 | 1975 |
| B | 50 | 1950 |
| C | 75 | 1925 |
| D | 100 | 1900 |
| E | 300 | 1700 |
| F | 500 | 1500 |

The following solutions were prepared for UV/VIS analysis:

PI2 Samples

TABLE 5

| Sample | Solution X (µl) | Buffer solution (µl) | Trypsin working solution (µl) | 0.001 N HCl (µl) |
| --- | --- | --- | --- | --- |
| 1-Blank | 0 | 200 | 0 | 200 |
| 2-Uninhibited | 0 | 200 | 100 | 100 |
| 3 | A(100) | 200 | 100 | 0 |
| 4 | B(100) | 200 | 100 | 0 |
| 5 | C(100) | 200 | 100 | 0 |
| 6 | D(100) | 200 | 100 | 0 |
| 7 | E(100) | 200 | 100 | 0 |
| 8 | F(100) | 200 | 100 | 0 |

TI Standards

TABLE 6

| Sample | Solution X (µl) | Buffer solution (µl) | Trypsin working solution (µl) | 0.001 N HCl (µl) |
| --- | --- | --- | --- | --- |
| 1-Blank | 0 | 200 | 0 | 200 |
| 2-Uninhibited | 0 | 200 | 100 | 100 |
| 3 | A(100) | 200 | 100 | 0 |
| 4 | B(100) | 200 | 100 | 0 |
| 5 | C(100) | 200 | 100 | 0 |
| 6 | D(100) | 200 | 100 | 0 |
| 7 | E(100) | 200 | 100 | 0 |
| 8 | F(100) | 200 | 100 | 0 |

The samples were allowed to equilibrate for 15 min. After equilibration, 2.3 ml of buffer solution were added. Just prior to reading samples, 300 µl of TAME solution were added. The sample was then vortexed and immediately transferred to a cuvette (1 cm pathlength). The samples were read at 247 nm at 10 second intervals for 3 minutes, and the reported inhibition rate (AU/min) was recorded. Negative controls consisting of TI standards or PI2 stock solution that have been heated for 1 hour at 110° C. can be included, but are not necessary. Previous work has shown that in comparison to buffer solutions, these inactivated protein solutions have no trypsin inhibition.

The following calculations are used:

1) Net uninhibited rate ($\Delta A_{247}$/min)=Uninhibited rate–Blank rate
2) Net inhibited rate ($\Delta A_{247}$/min)=Inhibited rate–Blank rate
3) Trypsin in reaction mix(mg)=Trypsin stock conc (mg/ml)/1000
4) Lyophilized solid (µg)=Solid (mg)*PI2 stock added to work sol'n (ml)*5
5) PI2 (µg)=(Solid (mg)*PI2 stock added to work sol'n (ml)* % purity)/20
6)

$$\text{Trypsin activity (units/mg enzyme)} = \frac{\text{Net rate } (\Delta A_{247}/\text{min}) * 1000 * 3}{540 * \text{trypsin in rxn mixture (mg)}}$$

(The extinction coefficient of Nα-p-Tosyl-L-arginine=540 ("Trypsinogen-Trypsin." Ed. Charles C. Worthington. *Worthington Enzyme Manual*. Freehold, N.J.: Worthington Biochemical Corporation, 1988. 320–324))

7) Net Remaining Trypsin Activity in each sample or standard (units)=Remaining Activity–Activity in Blank
8) Plots of trypsin activity vs. PI2 and/or lyophilized solids, proteins or PI2 (mg) were constructed. The point on the graph at which the activity has been reduced by ~50% is selected. The determined activity at this point and the amount of lyophilized solid, proteins or PI2 in the reaction mixture can be used to express the results as mg Trypsin Inhibited/mg Lyophilized Solid
mg Trypsin Inhibited/mg Proteins
mg Trypsin Inhibited/mg PI2 according to the following formulas:

8a) mg Trypsin Inhibited=(Net Total Uninhibited Activity−Net Remaining Uninhibited Activity)*trypsin in rxn mixture (mg)

8b)

$$\text{mg Trypsin Inhibited/mg Lyophilized Solid} = \frac{\text{mg Trypsin Inhibited} * 1000\ \mu g/mg}{\mu g\ \text{solid in rxn mixture}}$$

8c)

$$\text{mg Trypsin Inhibited/mg PI2} = \frac{\text{mg trypsin inhibited} * 1000\ \mu g/mg}{\mu g\ \text{PI2 in rxn mixture}}$$

In this assay a trypsin inhibitor unit was defined as the amount of the trypsin inhibitor that caused inhibition of 50% of the 0.2865 units of trypsin used in the reaction mixture, under the conditions applied for the reaction. This value will be taken from the standard inhibitor/inhibition curve. In the end, results were reported as units of trypsin inhibition/ mg solids or proteins.

Experiment 1

The temperature required to denature and precipitate protein impurities was first examined. A lot of potatoes was extracted and filtered using an extractant consisting of 1.0 N sodium chloride and 1.5% formic acid. This extract was filtered and aliquoted for the heat-treatment study. Each sample of the extract was placed in a test tube, and then heated to the target temperature using a constant temperature water bath. Samples were taken at times 0 minutes, 15 minutes, 30 minutes, 45 minutes and 60 minutes. The samples were immersed in an ice bath and then centrifuged in an Eppendorf 5415 centrifuge for 5 minutes at 10,000 rpm to remove precipitated material. The supernatant was analyzed using the reverse phase HPLC method described above and the Kunitz peaks were quantified. The results are reported in Table 7.

TABLE 7

Kunitz Impurities Remaining in Solution

| Temperature ° C. | Time (minutes) | Kunitz[1] mg/ml |
|---|---|---|
| 70 | 0 | 0.819 |
| 70 | 15 | 0.158 |
| 70 | 30 | 0.128 |
| 70 | 45 | 0.119 |
| 70 | 60 | 0.110 |
| 80 | 0 | 0.874 |
| 80 | 15 | 0.131 |
| 80 | 30 | 0.105 |
| 80 | 45 | 0.101 |
| 80 | 60 | 0.095 |
| 90 | 0 | 0.878 |
| 90 | 15 | 0.112 |
| 90 | 30 | 0.108 |
| 90 | 45 | 0.100 |
| 90 | 60 | 0.099 |

[1] The value for the Kunitz impurity is the summation of all protein eluting after the carboxypeptidase doublet using the reverse phase-HPLC methodology described in detail below.

It is clear from the data that there is a time advantage to be gained, in terms of rapidity of impurity removal, by treating the product at a temperature of 90° C. After 15 minutes at 90° C. the removal of the Kunitz type proteins was equivalent to that of heating for 60 minutes at 70° C. or heating for 30 minutes at 80° C. Unfortunately, as PI-2 has limited stability at 90° C., it is necessary to treat at a lower temperature to minimize PI2 degradation and loss. Removal of the Kunitz type proteins was efficiently accomplished by increasing the product temperature to 70° C. for 60 minutes. Heating the extract to 70° C. for 15 minutes generated an 81% reduction in the amount of Kunitz proteins and after 60 minutes at 70 ° C. this reduction had reached of 87%.

A further trial was run to determine the effect of heat treatment at various temperatures and time periods on the amount of PI2, carboxypeptidase inhibitor (CPI), Kunitz type proteins and overall purity. The conditions and results are as reported in Table 8.

TABLE 8

Protein purities of temperature trials from 60° C. through 80° C.

| Sample | PI2 (mg/ml) | CPI (mg/ml) | Kunitz (mg/ml) | Overall purity | PI2/Kunitz Purity |
|---|---|---|---|---|---|
| HT 60° C. 0 min | 0.27 | 0.22 | 1.32 | 14.70% | 16.75% |
| HT 60° C. 15 min | 0.26 | 0.22 | 0.77 | 20.74% | 25.28% |
| HT 60° C. 30 min | 0.25 | 0.22 | 0.64 | 22.61% | 28.18% |
| HT 70° C. 15 min | 0.21 | 0.19 | 0.29 | 29.93% | 41.58% |
| HT 70° C. 30 min | 0.21 | 0.20 | 0.13 | 38.18% | 61.49% |
| HT 80° C. 15 min | 0.24 | 0.22 | 0.19 | 36.82% | 55.35% |
| HT 80° C. 30 min | 0.24 | 0.22 | 0.26 | 33.48% | 48.25% |

Data in Table 8 provide supporting evidence of the use of a product temperature of 70° C. to maximize product purity. Of particular interest is the marked reduction in purity associated with the data taken at 60° C. This can possibly be explained by the incomplete precipitation of the Kunitz impurities below 70° C.

Experiment 2

Trials were conducted to determine the selection of an ultrafiltration system and operating conditions which would be effective at removing the Bowman-Birk and carboxypeptidase inhibitors without removing an excess of PI2. Three different filter types were examined, the Pall Filtron Centramate CS010C12, (Pall Corporation, East Hills, N.Y.), the Pall Filtron Maximate CS010G02, and the A/G Technology UFP-5-C-4A, (A/G Technology Corporation, Needham, Mass.). Each filter was tested under a range of conditions consistent with its specifications. All of the filters were found to be non-fouling under the tested conditions, but the Maximate filter had an average flux of 63 liters/hour/meter$^2$, compared to 54.7 for the Centramate and 20.2 for the A/G Technology filter.

Relative recovery of the PI2 after ultrafiltration was examined. While the A/G Technology membrane is rated at a molecular cutoff of 5000 Daltons and the Pall Filtron membrane is rated at 10,000 Daltons, the percentage of PI2 recovery was 7.60 for the A/G Technologies membrane and 9.61 for the Poll Filtron membrane. It is believed that differences in pore geometries of the Pall Filtron cellulosic membrane and the A/G Technolgy polysulfone membrane result in differences in filtration that are dependent on molecular geometry in addition to molecular weight. Tests using a membrane having a molecular cutoff of 1000 Daltons resulted in a dramatic reduction in flux.

Diafiltration against water resulted in rapid and irreversible fouling of the membrane with a corresponding flux rate decay. The use of a 100 mM ammonium bicarbonate buffer during the diafiltration phase prevented fouling of the membrane and allowed for the removal of the Bowman-Birk and carboxypeptidase inhibitors. Integration of the HPLC chromatographs prior to and after ultrafiltration/diafiltration demonstrated that the heat stable impurities were present at about one-third of the concentration of PI2. Ultrafiltration did not significantly change the ratio of impurity to PI2. Diafiltration against 6 volumes of 100 mM ammonium bicarbonate results in a reduction of the ratio of impurity to PI2 of greater than 50% (Table 9). Diafiltration against larger volumes of ammonium bicarbonate exhibited almost complete removal of the impurities after 20 volumes. The ratio of impurities to PI2 was observed to remain essentially unchanged when using water in place of the filtration buffer.

TABLE 9

Effect of Diafiltration with 100 mmol Ammonium Bicarbonate

| Sample | PI2 Integrated Area (mAU) | Doublet Impurity Integrated Area (mAU) | Ratio Impurity: PI2 |
|---|---|---|---|
| Heat Treated Extract | 2917 | 1119 | 0.384 |
| Concentrated Extract | 17133 | 6574 | 0.384 |
| 6X Diafiltered against AMBI | 25166 | 3767 | 0.150 |
| 10X Diafiltered against AMBI | 13967 | 1135 | 0.081 |
| 20X Diafiltered against AMBI | 17965 | 281 | 0.016 |

TABLE 9-continued

Effect of Diafiltration with 100 mmol Ammonium Bicarbonate

| Sample | PI2 Integrated Area (mAU) | Doublet Impurity Integrated Area (mAU) | Ratio Impurity: PI2 |
|---|---|---|---|
| ~5X Diafiltered against Water | 4648 | 1596 | 0.343 |

The heat treatment step denatures the Kunitz impurities and they are precipitated and removed by centrifugation. The carboxypeptidase inhibitor is known to have a heat stability similar to that of PI2 and so is not believed to be substantially denatured during the heat treatment step. While the heat stability of the Bowman-Birk impurities is not well-characterized, it may be assumed that some may be denatured and precipitated during the heat treatment step, but others may remain in the extract after centrifugation. Protease inhibitor II has a molecular weight of approx. 20,700 Daltons, Bowman-Birk have a molecular weight of approx. 8000 Daltons, and carboxypeptidase inhibitor has a molecular weight of approx. 4100 Daltons.

Six samples of PI2 extracted from potato tubers following the method described above were prepared. Each of the samples was separated using the reverse phase-HPLC method described above, with the following modifications: (a) the column used was a Microsorb C-4 (otherwise unchanged); (b) solvent A comprised 900 g DI $H_2O$ and 0.90 trifluoroacetic acid; and (c) the solvent composition was 80% A in the first and last 10 minute periods and 30% A in the 10 to 15 minute period. In each separation, three fractions were collected and retained, referred to as the fractions F1, F2, and F3 of FIG. 5, taken at time intervals of 17–32.5 minutes, 32.5–36 minutes, and 36–46 minutes, respectively. Note the carboxypeptidase inhibitor doublet at 36–38 minutes.

The volume of each F2 sample was reduced to 500 1 using a Roto-Vap under reduced pressure. Each of the samples was then separated using gel filtration-HPLC according to the previously described method. In each separation, three fractions were collected and retained, referred to as fractions F1, F2, and F3 of FIG. 5, taken at time intervals of 10–29.6 minutes, 29.6–34.5 minutes, and 34.5–70 minutes, respectively.

Following reverse phase chromatography of a sample using the previous procedure, the PI2 F2 peak (FIG. 5) was collected. The sample was reduced to approximately 100 μl using a Rotovap and deionized water was added to bring the volume to 500 μl. A manual injector was used to inject the sample into the GFC column. The chromatogram following gel filtration HPLC is illustrated in FIG. 6 (note that the peak at 36 minutes is an artifact). Expressing the TI results vs. PI2 protein content based on the GFC peak area showed an increase of ~35 times in the specific activity of the PI2 (Table 10).

TABLE 10

Trypsin activity exhibited by various PI2 preparations expressed by various means
TI Activity ( /mg)

| Sample | Solids | PI2 in F2 | Actual PI2 (GFC) |
|---|---|---|---|
| 1/22/01UF | 76.34 | 1960.78 | 384.62 |
| bulk batch #1 | 54.05 | 1960.78 | 476.19 |

TABLE 10-continued

Trypsin activity exhibited by various PI2 preparations expressed by various means
TI Activity ( /mg)

| Sample | Solids | PI2 in F2 | Actual PI2 (GFC) |
|---|---|---|---|
| 1/12/01UF | 32.26 | 1428.57 | 322.58 |
| 12/12/01UF | 76.34 | 3846.15 | 526.32 |
| 12/9/01UF | 31.75 | 2127.66 | 322.58 |
| 12/29/01UF | 74.07 | 1000.00 | 210.53 |
| average | 57.47 | 2053.99 | 373.80 |
| std dev | 21.43 | 973.31 | 114.69 |
| range: | 31.75–76.34 | 1428.57–3846.15 | 210.53–526.32 |

Trypsin inhibition activity was detected in all of the three peaks separated by GFC-HPLC. However the inhibition activity detected in the early and late eluting peaks was less than the inhibition levels detected in the GFC PI2 peak. Once present together, proteins eluting in other peaks such as those eluting in peak 1 and peak 3 may work in synergy with proteins from GFC PI2 peak. Variability among inhibition results was still observed in the GFC PI2 product. However, as can be depicted from the trypsin inhibitor activity content shown in Table 10, this variability was less than what was observed by expressing the results vs. solids or calculated PI2 content based on the GFC peak area. The trypsin inhibition activity content in the GFC PI2 peak was about 20% of the content determined based on calculated PI2 content in the same peak (Table 10). This is probably due to elution of trypsin inhibition activity that is not necessarily due to PI2, under the early and late appearing peaks separated by RP-HPLC (FIG. 5) and/or GFC-HPLC. This interpretation is partially supported by the fact that various protein levels were detected in the three peaks separated by GFC-HPLC (Table 11).

TABLE 11

Protein content in various PI2 product fractions

| | total solids (mg) | Bradford based total protein (mg)* | Total Protein content in GFC peaks (mcg) | Bradford based actual proteins in GFC F1 (mcg) | actual proteins in GFC F2 (mcg)** | actual proteins in GFC F3 (mcg) |
|---|---|---|---|---|---|---|
| 1/22 | 5.25 | 0.743 (14.13%) | 195.8 | 40.2 (21.1%) | 118.6 (60.6%) | 37.2 (20%) |
| bulk batch #1 | 5.25 | 0.704 (13.42%) | 155.7 | 38.1 (24.5%) | 63.5 (40.8%) | 54.6 (35.1%) |
| 1/12 | 5.25 | 0.698 (13.30%) | 140.3 | 35.5 (25.3%) | 86.7 (61.8) | 18.1 (12.9%) |
| 12/12 | 5.25 | 0.961 (18.30%) | 149.9 | 47.3 (31.6%) | 66.5 (44.4%) | 36.1 (24.1%) |
| 12/9 | 5.25 | 0.803 (15.29%) | 213 | 60.6 (28.5%) | 108.1 (50.8%) | 44.3 (20.8%) |
| 12/29 | 5.25 | 0.760 (14.48%) | 205.2 | 53.6 (26.1%) | 92.5 (26.1%) | 59.1 (28.8) |

*= total protein/total solids
**= Proteins in GFC peaks/Total protein content

Experiment 3

Figure 5:
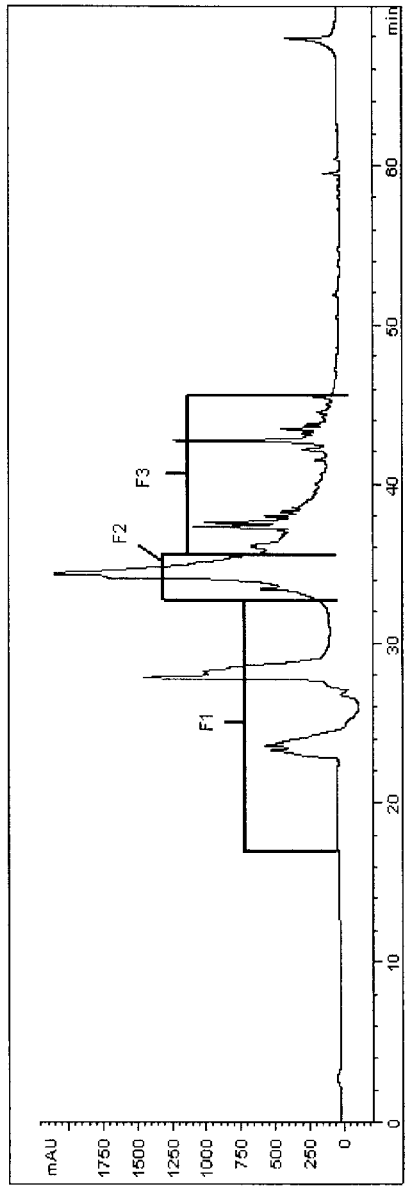
FIG. 5 is a chromatogram of the purified protease inhibitor II peak (i.e., F2) following removal of the Kunitz inhibitors made using reverse phase HPLC.
Figure 6:
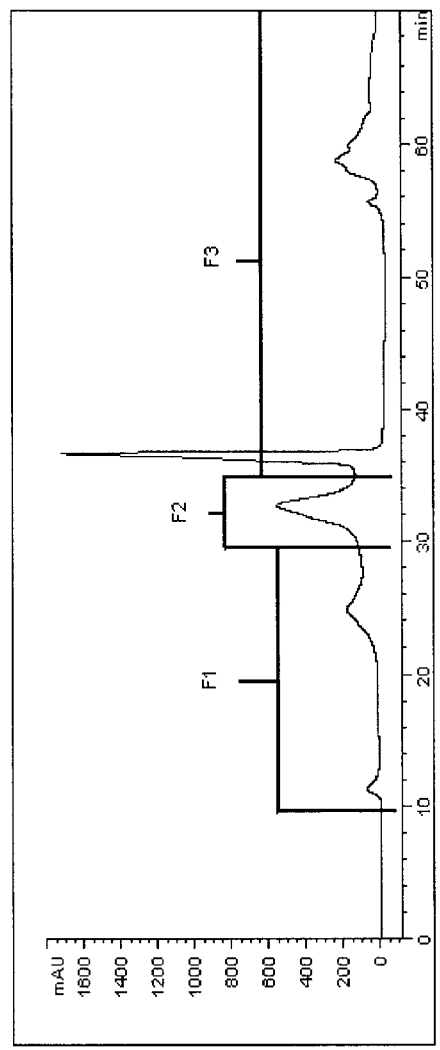
FIG. 6 is a chromatogram of the F2 fraction of FIG. 5 made using gel filtration HPLC.

To verify that the peak in the F2 region of FIG. 5 contains potato PI2, a sample of PI2 was obtained from Dr. Clarence Ryan at Washington State University. The sample of PI2 was prepared by Dr. Ryan's laboratory following the method described in Melville et al. The PI2 standard and a sample of the purified PI2 extract produced using the method of this specification were analyzed using the gel electrophoresis method described above. Also run on the gel were molecular weight standards, including Lactalbumin (MW=14,400) and soybean trypsin inhibitor (MW=20,100). The PI2 standard showed a band in agreement with a band of the PI2 sample of the present invention. Moreover, there were no bands prior to the Lactalbumin standard marker band at 14,400 Daltons. Accordingly, the gel electrophoresis results demonstrate that the F2 region of FIG. 5 includes the PI2 extracted from the potatoes.

Figure 4:
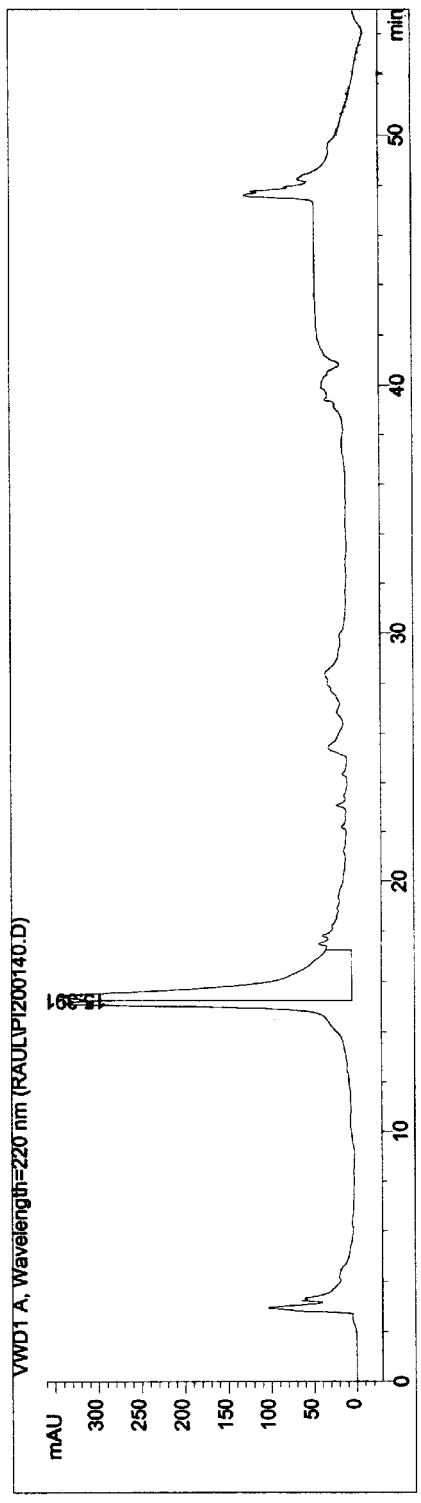
FIG. 4 is a chromatogram of the purified PI2 extract of the present invention made using reverse phase HPLC under the same conditions as FIGS. 1–3.
Figure 7:
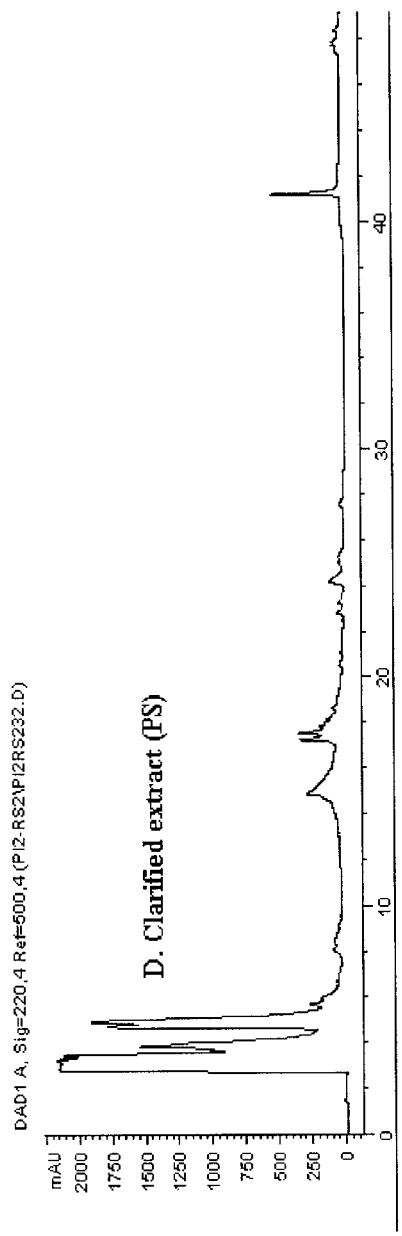
FIG. 7 is a chromatogram of the protein extract after heat treatment and clarification but before filtration.
Figure 8:
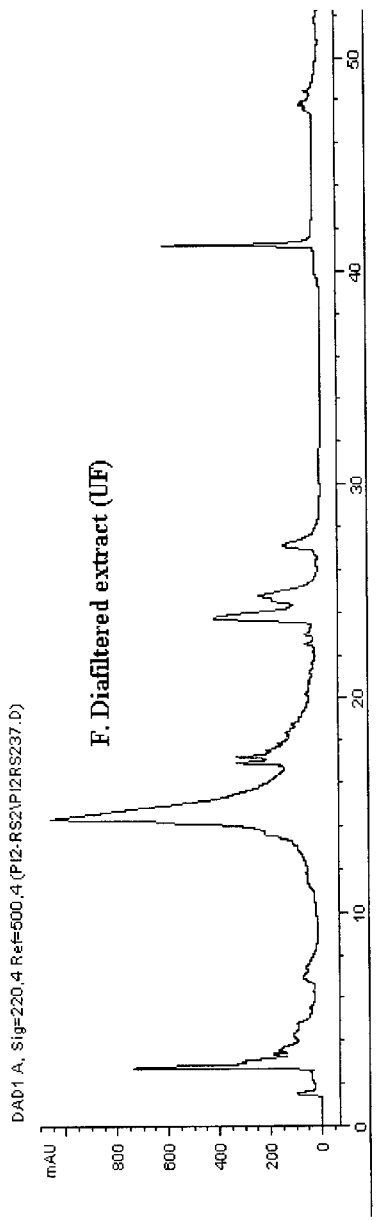
FIG. 8 is a chromatogram of the protein extract of FIG. 7 after filtration.

To verify the removal of the impurities, the reverse phase HPLC method was used to analyze a sample of the purified PI2 extract. A chromatogram of the PI2 sample is illustrated in FIG. 4. The principal peak at 15.4 minutes is the peak containing the PI2. Based on the analysis of the carboxypeptidase standard (FIG. 3) and the Kunitz standard (FIG. 1), very little of the impurities show up on the HPLC chromatogram of FIG. 4, except for a small amount of the carboxypeptidase doublet that can be seen at approximately 18 minutes, and a small amount of the Kunitz peak that can be seen at approximately 25 minutes. The effect of filtration on the removal of the CPI is illustrated in the two HPLC chromatograms of FIGS. 7 and 8. The peak at approximately 15 minutes is the PI2 peak, with the CPI doublet appearing at 17–18 minutes. The dramatic reduction in the size of the CPI doublet is clearly shown by the relative changes in the PI2 peak and the CPI doublet.

As demonstrated in FIG. 2, the Bowman-Birk standard elutes under reverse phase HPLC at approximately the same time as the PI2 peak of FIG. 4. Accordingly, HPLC could not be used, as with Kunitz and carboxypeptidase, to demonstrate removal of Bowman-Birk impurities. Note, however, that the gel electrophoresis pattern reported above showed no bands smaller than 14,400 Daltons. Since the Bowman-Birk impurities are known to have a molecular weight of approximately 8,000 Daltons, the gel electrophoresis results demonstrate removal of the Bowman-Birk impurities. Further, since the carboxypeptidase impurities have a molecular weight of 4,100 Daltons, the gel electrophoresis results also support the removal of the carboxypeptidase impurities.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claim are so limited. Those skilled in the art who have the disclosure before them will be able to make modifications and variations therein without departing from the scope of the invention.

We claim:

1. A method of removing Kunitz, Bowman-Birk and carboxypeptidase inhibitors from protease inhibitor II-containing plant material, comprising the steps of:

(a) extracting protease inhibitors from the plant material using an alcohol-free, aqueous solvent comprising an organic acid and between about 2 weight percent and about 20 weight percent sodium chloride to form an extract containing the protease inhibitor II and the Kunitz, Bowman-Birk and carboxypeptidase inhibitors;

(b) heating the extract to a temperature between about 65° C. and about 90° C. for between about 15 minutes and about 180 minutes to denature the Kunitz inhibitors;

(b) cooling the extract to between about 20° C. and about 30° C.;

(c) centrifuging the cooled extract to remove the denatured Kunitz inhibitors and form a clarified extract;

(d) using ultrafiltration in the presence of a buffer to remove the Bowman-Birk and carboxypeptidase inhibitors from the clarified extract.

2. The method of claim 1, wherein the buffer comprises ammonium bicarbonate.

3. The method of claim 1, wherein the heating temperature is between about 68° C. and about 73° C. and the heating time is between about 45 and about 75 minutes.

4. The method of claim 1, wherein the organic acid is formic acid.

* * * * *

UNITED STATES PATENT AND TRADEMARK OFFICE
CERTIFICATE OF CORRECTION

PATENT NO.    : 6,686,456 B2
DATED         : February 3, 2004
INVENTOR(S)   : Ausich et al.

It is certified that error appears in the above-identified patent and that said Letters Patent is hereby corrected as shown below:

Title page,
Item [73], Assignees, should read:
-- Kemin Consumer Care, L.C.
Des Moines, Iowa (US) --
Item [75], Inventor, should read:
-- Brent Davidson
Ankeny, Iowa (US) --

Signed and Sealed this

Sixth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,686,456 B2
APPLICATION NO. : 09/900550
DATED : February 3, 2004
INVENTOR(S) : Ausich et al.

It is certified that error appears in the above-identified patent and that said Letters Patent is hereby corrected as shown below:

Item [75], Inventor, should read
--Brent Davison
Ankeny, Iowa (US)--

Signed and Sealed this

Twenty-ninth Day of August, 2006

JON W. DUDAS
*Director of the United States Patent and Trademark Office*